United States Patent
Lindell et al.

(10) Patent No.: US 12,285,520 B2
(45) Date of Patent: *Apr. 29, 2025

(54) PRODUCT AND MANUFACTURING PROCESS FOR A GUM

(71) Applicant: McNeil AB, Helsingborg (SE)

(72) Inventors: Katarina Lindell, Eslöv (SE); Kristina Thyresson, Lund (SE); Jill Nilgard, Helsingborg (SE); Martin Edman, Klippan (SE)

(73) Assignee: McNeil AB, Helsingborg (SE)

( * ) Notice: Subject to any disclaimer, the term of this patent is extended or adjusted under 35 U.S.C. 154(b) by 498 days.

This patent is subject to a terminal disclaimer.

(21) Appl. No.: 17/758,710

(22) PCT Filed: Jan. 14, 2021

(86) PCT No.: PCT/EP2021/050698
§ 371 (c)(1),
(2) Date: Jul. 13, 2022

(87) PCT Pub. No.: WO2021/144365
PCT Pub. Date: Jul. 22, 2021

(65) Prior Publication Data
US 2023/0072107 A1 Mar. 9, 2023

(30) Foreign Application Priority Data
Jan. 15, 2020 (SE) .................................... 2050026-0

(51) Int. Cl.
*A61K 9/68* (2006.01)
*A23G 4/06* (2006.01)
(Continued)

(52) U.S. Cl.
CPC ............ *A61K 9/0058* (2013.01); *A23G 4/062* (2013.01); *A23G 4/10* (2013.01); *A61K 31/465* (2013.01); *A61K 2800/622* (2013.01)

(58) Field of Classification Search
CPC .... A61K 9/0058; A61K 31/465; A23G 4/062; A23G 4/10
See application file for complete search history.

(56) References Cited

U.S. PATENT DOCUMENTS

| 3,877,468 A | 4/1975 | Lichtneckert et al. |
| 5,976,581 A | 11/1999 | Song et al. |

(Continued)

FOREIGN PATENT DOCUMENTS

| FR | 2608156 A | 6/1988 |
| WO | WO 2000/035295 A | 6/2000 |

(Continued)

OTHER PUBLICATIONS

SE search report and written opinion dated Aug. 10, 2020, for corresponding SE 2050026-0.
(Continued)

*Primary Examiner* — Trevor Love (57) ABSTRACT

The invention relates to a nicotine chewing gum giving an immediate release and uptake of nicotine as well as an extended release and uptake of nicotine as well as describing suitable manufacturing processes for such chewing gum formulations and the use of the chewing gum for the treatment of a human being suffering from cravings from tobacco and/or e-cigarette dependency.

16 Claims, 3 Drawing Sheets

(51) Int. Cl.
*A23G 4/10* (2006.01)
*A61K 31/465* (2006.01)

(56) References Cited

U.S. PATENT DOCUMENTS

| | | |
|---|---|---|
| 2002/0002189 A1 | 1/2002 | Smith et al. |
| 2004/0194793 A1 | 10/2004 | Lindell et al. |
| 2006/0275344 A1* | 12/2006 | Mody .................. A61K 9/0058 424/439 |
| 2013/0209540 A1 | 8/2013 | Duggins et al. |
| 2017/0224671 A1 | 8/2017 | Nielsen |

FOREIGN PATENT DOCUMENTS

| | | |
|---|---|---|
| WO | WO 2006/000232 A | 1/2006 |
| WO | WO 2006/124366 A | 11/2006 |
| WO | WO 2007/133140 A | 11/2007 |
| WO | WO 2009/080020 A | 7/2009 |
| WO | WO 2009/141321 A | 11/2009 |
| WO | WO 2010/044736 A | 4/2010 |
| WO | WO 2011/038070 A | 3/2011 |

OTHER PUBLICATIONS

International search report and written opinion dated May 11, 2021, for corresponding PCT/EP2021/050698.

* cited by examiner

PRODUCT AND MANUFACTURING PROCESS FOR A GUM

CROSS-REFERENCE TO RELATED APPLICATIONS

This application is the national stage filing under 35 USC 371 of international application PCT/EP2021/050698 filed on Jan. 14, 2021, which claims priority to SE 2050026-0 filed on Jan. 15, 2020, the complete disclosures of which are hereby incorporated herein by reference for all purposes.

FIELD OF INVENTION

This invention relates to a nicotine chewing gum giving an immediate release and uptake of nicotine and an extended release and uptake of nicotine as well as describing suitable manufacturing processes for such chewing gum formulations and the use of the chewing gum for the treatment of a human being suffering from cravings from tobacco and/or e-cigarette dependency.

BACKGROUND OF INVENTION

According to WHO about six million people die from smoking related diseases each year, even though there are products (medicines) on the market to help a smoker to quit smoking; products such as e.g. nicotine comprising chewing gums, lozenges, sprays and transdermal patches.

A traditional way to produce a nicotine chewing gum is to create a complex of nicotine with a cation exchange resin and to add this complex to a chewing gum formulation.

Such chewing gums are available on the market since many years, sold under, for example the trade mark Nicorette®. However, there are consumers that are looking for nicotine products (medicines) that could provide faster craving relief, closer to the craving relief of a cigarette and thus there is still an opportunity to develop new nicotine chewing gums that could satisfy this population using tobacco and/or e-cigarettes.

One product on the market giving rise to a faster craving relief is the Nicorette™ QuickMist™ which is a mouth spray to be applied to the oral mucosa from which the nicotine compound is readily absorbed into the blood stream to give a fast craving relief.

WO2006124366 discloses a chewing gum comprising at least a nicotine resin within a core wherein at least one inner polymer film coating is applied thereon and at least one outer hard coating. The gum formed exhibits a long-lasting effect of flavorings and gives a sustained release of nicotine when the subjects are chewing on the gum.

WO2010044736 discloses a multi portion intra-oral lozenge dosage form where at least one portion is rapidly disintegrating and at least one portion is slowly disintegrating wherein nothing is mentioned about a chewing gum. There are long lists of active pharmaceutical agents that can be suitable and lists of diseases.

The problem to be solved by this invention is to provide a product that could give a fast uptake of nicotine as well as an extended release of nicotine to aid a person to stop smoking. To be able to achieve such an effect it is important to include nicotine as well as a buffer in a format that will give rise to a fast uptake of nicotine, in addition to the sustained/extended release performance which is already commonly applied for nicotine containing medicated chewing gums.

However, there are consumers who could benefit from products that could provide both a fast and more prolonged craving relief, from one and the same product.

SUMMARY OF THE INVENTION

The inventors have been exploring the possibility to create a chewing gum giving rise to an immediate as well as an extended release and uptake of nicotine, which still has good taste and palatability. To provide an immediate release and uptake from a nicotine gum product, the inventors approach has been to apply nicotine in a more readily available nicotine salt form, such as nicotine bitartrate or nicotine ditartrate dihydrate comprised in at least one outer portion/layer fused onto the outside of a hard-coated nicotine chewing gum.

The pKa for nicotine is approximately 7.8. It is well known that the uncharged (free base form) could more easily and faster enter biological membranes, such as the oral mucosa, in order to obtain a fast systemic uptake, compared to the nicotine in its positively charged acid form.

Thus, if an acid drug salt like nicotine bitartrate is co-formulated in a product in such a way that the product also contains some readily available and fast released buffer (s), which also are present outside of a hard-coated nicotine chewing gum. These buffer(s) could rapidly and transiently increase the pH of the solvent (in this case saliva) in order to convert nicotine into its' free base form which would result in a relatively faster absorption of the nicotine being present in at least one portion/layer outside of a hard-coated chewing gum core.

The average pH of the human saliva is normally just about 6-7.5.

By selecting and adding some readily and fast released buffer(s) to the parts outside thehewing gum core, a fast pH increase of the saliva of approximately one pH unit above the pKa of nicotine (thus in the range of at or above pH 9) could be achieved. This would result in that approximately about 90% of the nicotine in the at least one portion/layer would be converted to its' free base form after disintegration and dissolution of the at least one portion/layer in the saliva to be readily absorbed into the systemic circulation to provide for a faster craving relief.

Nicotine free base form is not suitable to directly be formulated into semisolid or solid dosage forms since the nicotine base form is in a highly volatile liquid form at normal conditions.

To be able to provide a transient and suitable pH increase there is a benefit of using a buffering system, such as one or more different buffer(s) (buffer species). Normally, buffering systems do not taste well and thus they need to be selected carefully and taste masked by e.g. sweeteners and flavors. In addition, the buffering capacity of one buffer (buffer species) might not be sufficient.

To provide an extended release of nicotine from a nicotine chewing gum core, the use of nicotine bound to a resin such as nicotine polacrilex is suitable. Nicotine polacrilex is normally used in the medicated chewing gums available on the market. Such a medicated chewing gum would provide an extended release over a time up to about 20 to 45 minutes, depending on the usage. However, the release and uptake from these gums during the first 5-10 minutes of usage is somewhat limited.

The invented nicotine chewing gum provides new features in one and the same product, compared to other currently available commercialized medicinal nicotine products.

The nicotine chewing gum could also become an attractive product for consumers or patients that prefer nicotine chewing gums as a format.

In a first aspect this invention relates to a nicotine chewing gum comprising
i. a gum core comprising nicotine,
ii. optionally a polymer based film coating comprising at least one flavor and at least one sweetener covering the chewing gum core,
iii. at least one polyol-based hard coating covering the chewing gum, comprising at least one sugar alcohol or mixtures of sugar alcohols,
iv. at least one portion/layer fused onto the outside of the polyol-based hard coating, wherein the portion/layer comprises nicotine salt and at least one sugar alcohol or a mixture of sugar alcohols,
v. at least one portion/layer fused onto the outside of the polyol-based hard coating, wherein the portion/layer comprises one or more buffer(s) in an amount of from about 3 mg to about 7.5 mg and at least one sugar alcohol or a mixture of sugar alcohols,
and
wherein the nicotine release from the at least one outer portion/layer (iv) is immediate and the nicotine release from the core (i) is extended
and
wherein the buffer(s) (v) located outside the hard-coated gum promotes a rapid uptake of nicotine from (iv) through the oral mucosa.

In a second aspect the invention relates to a nicotine chewing gum comprising,
i. a gum core comprising nicotine,
ii. at least one film coating covering the gum core comprising at least two buffers, and at least one film forming polymer
or at least one film coating covering the gum core comprising at least two buffers, at least one sweetener, at least one flavor, and at least one film forming polymer and at least one film forming polymer,
or at least two film coating covering the gum core, wherein one film coating comprises at least two buffers and at least one film forming polymer and another film coating comprises at least one sweetener, at least one flavor, and at least one film forming polymer and at least one film forming polymer,
iii. at least one polyol-based hard coating covering the at least one film coating, wherein the polyol-based hard coating comprises at least one sugar alcohol or mixtures of sugar alcohols,
iv. at least one portion/layer fused onto the outside of the polyol-based hard coating, wherein the portion comprises nicotine salt, and at least one sugar alcohol or a mixture of sugar alcohols
and
wherein the nicotine release from the at least one outer portion/layer (iv) is immediate and the nicotine release from the core (i) is extended
and
wherein the at least two buffers (ii) in the at least one film coating located outside the core promotes a rapid uptake of nicotine from (iv) through the oral mucosa.

Figure 1:
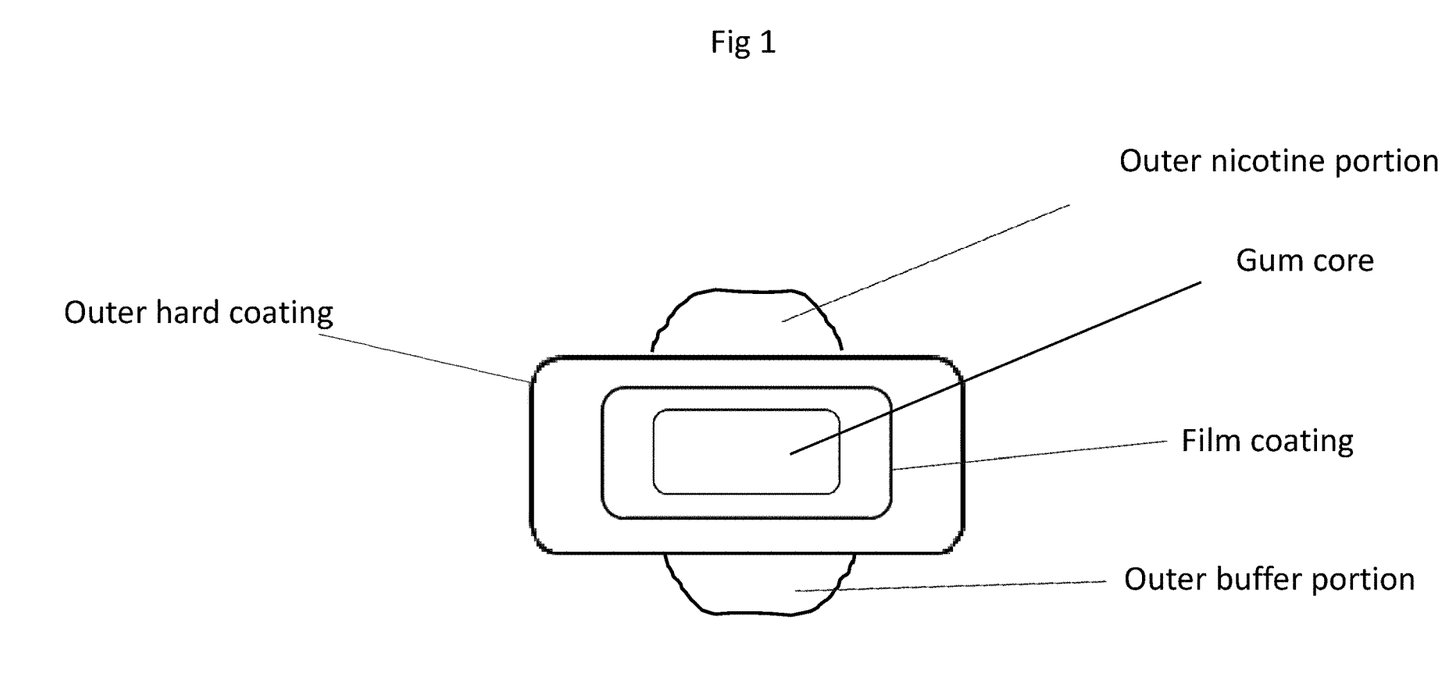
FIG. 1 shows one embodiment of a nicotine chewing gum according to the invention.

In another aspect the invention relates to a method of manufacturing a chewing gum, comprising the steps of;
i. providing a chewing gum core comprising nicotine,
ii. providing a polymer based film coating formulation including at least one flavor and at least one sweetener,
iii. coating the chewing gum core with the polymer based film formulation,
iv. obtaining a polymer based film coated chewing gum,
v. providing a polyol-based hard coating formulation comprising at least one sugar alcohol or mixtures of sugar alcohols,
vi. coating said chewing gum with said polyol-based hard coating formulation,
vii. obtaining a polyol-based hard-coated chewing gum,
viii. providing a composition comprising nicotine salt and at least one sugar alcohol or a mixture of sugar alcohols,
ix. fusing said composition from viii) onto the outside of the hard-coated chewing gum as at least one portion/layer obtaining a hard-coated chewing gum with at least one portion/layer containing nicotine salt,
x. providing a composition comprising one or more buffer(s) in an amount of from about 3 mg to about 7.5 mg and at least one sugar alcohol or a mixture of sugar alcohols,
xi. fusing said composition from x) onto the outside of the hard-coated chewing gum as at least one portion/layer obtaining a hard-coated chewing gum with at least one portion/layer containing one or more buffer(s),
and
wherein the nicotine release from the at least one outer portion/layer (ix) is immediate and the nicotine release from the core (i) is extended
and
wherein the one or more buffer(s) in at least one film coating (xi) located outside the hard-coated gum promotes a rapid uptake of nicotine through the oral mucosa (see for example FIG. 1).

Figure 2:
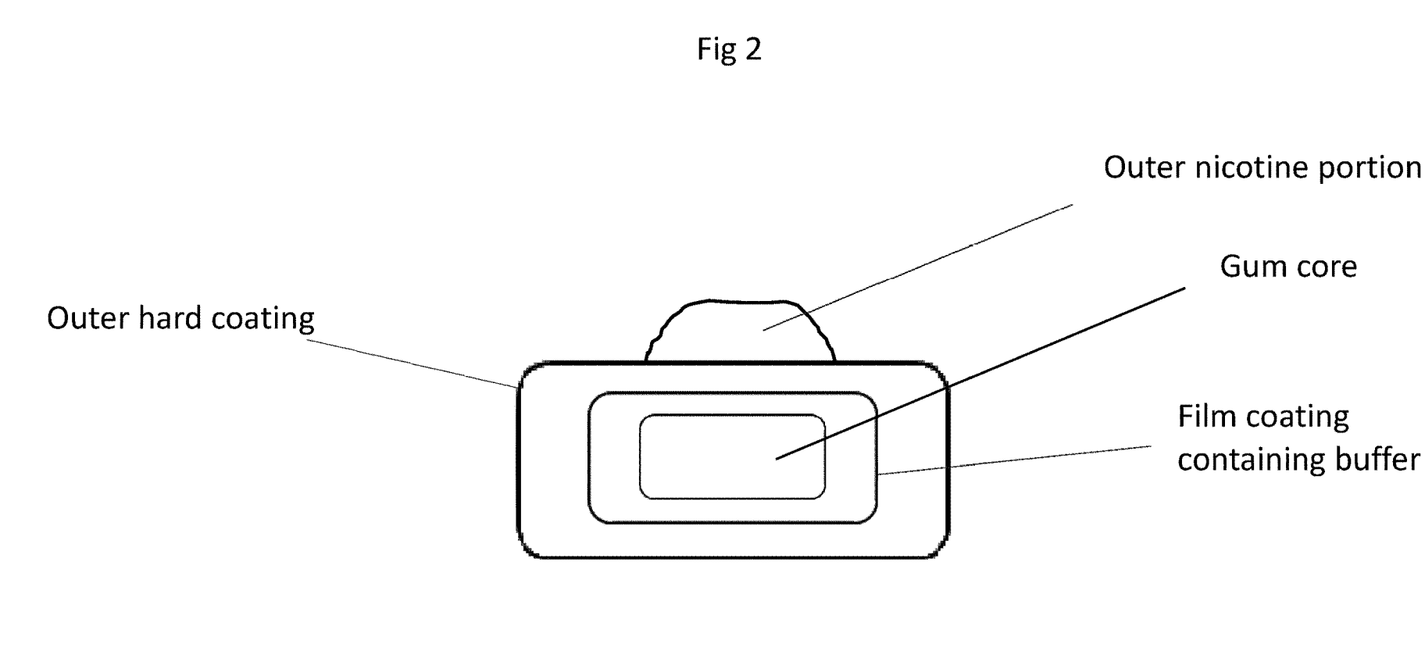
FIG. 2 shows one embodiment of a nicotine chewing gum according to the invention.

In another aspect the invention relates to a method of manufacturing a chewing gum, comprising the steps of
i. providing a chewing gum core comprising nicotine,
ii. providing a polymer based film coating formulation comprising at least two buffers and at least one sweetener and at least one flavor,
iii. coating said chewing gum core with the polymer based film coating formulation,
iv. obtaining a film coated chewing gum, comprising at least two buffers and at least one sweetener and at least one flavor,
v. providing a polyol-based hard coating formulation comprising at least one sugar alcohol or mixtures of sugar alcohols,
vi. coating said film coated chewing gum with said polyol-based hard coating formulation,
vii. obtaining a hard-coated chewing gum,
viii. providing a formulation comprising nicotine salt and at least one sugar alcohol or a mixture of sugar alcohols,
ix. fusing said composition from viii) onto the outside of the hard-coated chewing gum as at least one portion/layer obtaining a hard-coated chewing gum with at least one portion/layer containing nicotine salt and
wherein the nicotine release from the outer portion/layer (ix) is immediate and the nicotine release from the core (i) is extended
and
wherein the at least two buffers in the film coating (iv) located outside the gum core promotes a rapid uptake of nicotine through the oral mucosa (see for example FIG. 2).

Figure 3:
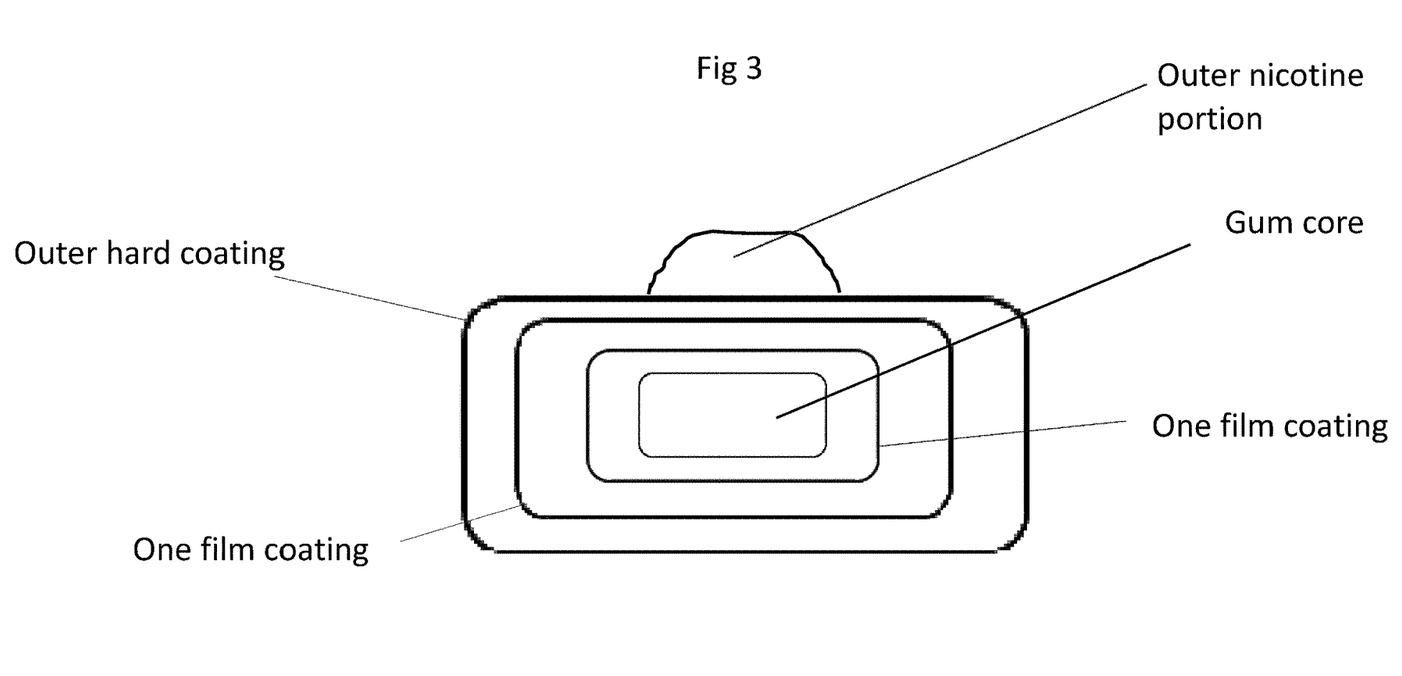
FIG. 3 shows one embodiment of a nicotine chewing gum according to the invention.

In another aspect the invention relates to a method of manufacturing a chewing gum, comprising the steps of;
i. providing a chewing gum core comprising nicotine,
ii. providing a polymer based film formulation comprising at least two buffers,
iii. coating said chewing gum core with said polymer based film formulation,
iv. obtaining a film coated chewing gum with a film coating comprising at least two buffers
v. providing a polymer based film formulation comprising at least one sweetener and at least one flavor,
vi. coating said chewing gum with said polymer based film formulation,
vii. obtaining a chewing gum coated with a polymer based film coating,
viii. providing a polyol-based hard coating formulation comprising at least one sugar alcohol or mixtures of sugar alcohols,
ix. coating said film coated chewing gum with said polyol-based hard coating formulation,
x. obtaining a hard-coated chewing gum,
xi. providing a composition comprising nicotine salt and at least one sugar alcohol or a mixture of sugar alcohols
xii. fusing said composition from xi) onto the outside of the hard-coated chewing gum as at least one portion/layer obtaining a hard-coated chewing gum with at least one portion/layer containing nicotine salt,
and
wherein the nicotine release from the outer portion/layer (xii) is immediate and the nicotine release from the core (i) is extended
and
wherein the at least two buffers (iv) in the film coating located outside the gum core promotes a rapid uptake of nicotine through the oral mucosa (see for example FIG. 3).

The steps mentioned above could be in any order. In one example a step of providing a polymer based film formulation comprising at least two buffers, at least one sweetener and at least on flavor replaces the two steps of providing the at least one buffer in one polymer based film formulation in one step and providing the at least one sweetener and at least one flavor in one polymer based film formulation in another step.

In a final aspect the invention relates to the use of the above described chewing gums for the treatment of a human being suffering from cravings from tobacco dependency and/or e-cigarette dependency, i.e., to help a human quitting smoking, vaping, using "snus" or chewing tobacco.

BRIEF DESCRIPTION OF THE DRAWINGS

There is no scaling in the drawings, and they are there to illustrate the invention.

DETAILED DESCRIPTION OF EMBODIMENTS OF THE INVENTION

Definitions

In the context of the present application and invention the following definitions apply:

The term "nicotine" refers to the amount (mg) of nicotine in any salt form or bound to any carrier calculated as the amount of corresponding free base per piece of gum.

The term "core or gum core" are intended to mean a chewing-gum based delivery system used to carry gum base, sweeteners, flavors, fillers and any other substances in chewing gum and bubble gum. It provides all the basic textural and masticatory properties of gum.

The term "portion/layer" is intended to mean a part that is fused or attached to the outside of the hard-coated chewing gum at any place. It might be in any kind of form including a round portion (dot), square portion, conic portion, triangle etc. The portion may be in the form of a trade mark as well as having a color. The portion may also be a layer present outside the hard coating of the gum, such as 40% of the gum surface for one layer, such as one side, or both sides of the gum.

The term "buffer(s)" refers to two different kinds of buffer species also differentiating the corresponding acid-base pair of a buffer system.

As used herein, the term "extended release" ("ER") refers to formulations which are characterized by that the nicotine present in the chewing gum core will be released over an extended period of mastication normally for 20-45 minutes, the time a consumer or patient is chewing on (using) the gum. The release profile may be assessed via in vitro dissolution using techniques known to those skilled in the art (European Pharmacopeia 9.0, General chapters, method of analysis, 2.9.25 Dissolution for medication chewing gums, apparatus B).

The term "immediate release" ("IR") as used herein is intended to mean the release of the nicotine comprised in the polyol (sugar alcohol) based portion(s)/layer(s) on the outside of the hard-coated gum aimed to be available for fast oromucosal absorption. The rate of release of nicotine is not prolonged by means of a controlled release matrix or other such means but it is dependent of the disintegration and dissolution of the portion(s)/layer(s) or film coatings and water solubility of the polyol and nicotine salt. As described herein, an "immediate release" component is released shortly after the sugar alcohol and nicotine mixture is disintegrated and dissolved (in the saliva) which occurs shortly after the chewing gum is administrated and mastication begins.

The calculation of the amount of nicotine present in the chewing gum core is calculated and most often expressed as the amount of the corresponding free base form of nicotine.

The term "fused onto" used throughout the application is intended to be interchangeable with "attached to", "fused to", "sticked to", "deposited onto", "applied to", "adhered to", or "melted onto" or "printed on".

The Chewing Gum

In one embodiment the invention relates to a nicotine chewing gum comprising
i. a gum core comprising nicotine
ii. optionally a polymer based film coating comprising at least one flavor and at least one sweetener covering the chewing gum core,
iii. at least one polyol-based hard coating covering the chewing gum, comprising at least one sugar alcohol or mixtures of sugar alcohols,
iv. at least one portion/layer fused onto the outside of the polyol-based hard coating, wherein the at least one portion/layer comprises nicotine salt and at least one sugar alcohol or a mixture of sugar alcohols,
v. at least one portion/layer fused onto the outside of the polyol-based hard coating, wherein the at least one portion/layer comprises one or more buffer(s) in an amount of from about 3 mg to about 7.5 mg and at least one sugar alcohol or a mixture of sugar alcohols, and wherein the nicotine release from the at least one outer portion/layer (iv) is immediate and the nicotine release from the core (i) is extended and wherein the buffer(s) (v) located outside the hard coated chewing gum promotes a rapid uptake of nicotine from (iv) through the oral mucosa (see for example FIG. 1).

The sugar alcohol present in the polyol-based portion(s) or layer(s) outside the hard coating comprises erythritol.

In another embodiment the invention relates to a nicotine chewing gum comprising, i. a gum core comprising nicotine, ii. at least one film coating covering the gum core comprising at least two buffers, and at least one film forming polymer or at least one film coating covering the gum core comprising at least two buffers, at least one sweetener, at least one flavor, and at least one film forming polymer and at least one film forming polymer, or at least two film coating covering the gum core, wherein one film coating comprises at least two buffers and at least one film forming polymer and another film coating comprises at least one sweetener, at least one flavor, and at least one film forming polymer and at least one film forming polymer, at least one film coating covering the gum core comprising at least two buffers, at least one sweetener, at least one flavor, and at least one film forming polymer, iii. at least one polyol-based hard coating covering the at least one film coating, wherein the polyol-based hard coating comprises at least one sugar alcohol or mixtures of sugar alcohols, iv. at least one portion/layer fused onto the outside of the polyol-based hard coating, wherein the portion comprises nicotine salt, and at least one sugar alcohol or a mixture of sugar alcohols and wherein the nicotine release from the at least one outer portion/layer (iv) is immediate and the nicotine release from the core (i) is extended and wherein the at least two buffers (ii) located in the at least one film coating promotes a rapid uptake of nicotine from (iv) through the oral mucosa (see for example FIGS. 2 and 3).

The sugar alcohol present in the polyol-based portion(s) or layer(s) outside the hard coating gum core comprises erythritol.

In one embodiment the one film coating comprises at least two buffers, at least one sweetener and at least one flavor.

In another embodiment two different polymer based film coatings are applied, the first coating being in contact with the gum core and the second film coating is placed outside the first film coating. The at least two buffers are present in one of the film coatings and at least one sweetener and at least one flavor are present in the other film coating. In one example, the buffers are present in the first film coating and the at least one sweetener and at least one flavor in the second film coating. In another example the at least one sweetener and at least one flavor are present in the first film coating and the at least two buffers present in the second film coating.

It is well known for a person skilled in the art how to produce a traditional chewing gum.

One example is the process disclosed in the U.S. Pat. No. 3,877,468. Coated chewing gums have been disclosed in WO2006/124366 wherein polyol-based hard coatings in combination with an inner polymer coating comprising one or more sweeteners and/or flavors were described to improve the taste and the sensory acceptance of the chewing gum.

The gum core comprises nicotine, such as nicotine bound to ion exchange resins, such as nicotine polacrilex, nicotine bound to zeolites and/or nicotine bound to beta cyclo dextrines, preferably in the form as nicotine polacrilex. The nicotine present in the chewing gum core (calculated as the free base) may be from about 1.0 to about 6.0 mg, about 2.0 to about 4.0 mg, such as 1.0, 1.25, 1.5, 1.75, 2.0, 2.25, 2.5, 2.75, 3.0, 3.25, 3.5, 3.75, 4.0, 4.25, 4.5, 5.0, 5.5 or 6.0, calculated per piece of gum. The nicotine will be released from the gum core when the user is chewing on the gum and the release will occur over an extended time period, normally up to about 30-45 minutes, which is the average time a consumer or patient is chewing on a nicotine chewing gum.

The at least two buffers can be present in the at least one film coating located outside the gum core, or the one or more buffers can be present in the at least one portions/layer fused to the outside of the hard-coated gum. The buffer(s) are selected from the group consisting of sodium carbonate, sodium bicarbonate, potassium carbonate, potassium bicarbonate, trometamol base (Tris base), or the corresponding conjugated acid of trometamol such as Trometamol hydrochloride (Tris HCl), trisodium phosphate, disodium hydrogenphosphate, sodium dihydrogen phosphate, tripotassium phosphate, dipotassium hydrogenphosphate, potassium dihydrogen phosphate and mixtures thereof.

In some examples the buffer(s) can either be present in the at least one film coating or in the at least one portion/layer outside the hard coated gum and selected from the group consisting of sodium carbonate, sodium bicarbonate, trometamol base (Tris base) or the corresponding conjugated acid of trometamol such as Trometamol hydrochloride (Tris HCl), and mixtures thereof.

The acidic nicotine salt and the alkaline buffers are not suitable to be present in the same or adjacent polymer based film coating or the same portion/layer outside the hard coated gum. Interaction during the drying and/or cooling process could lead to transformation of nicotine to the free base form which is a volatile and unstable liquid, thus resulting in loss of nicotine or a chemically unstable product.

The buffer(s) in the film coating may be present in a total amount from about 1.0 to about 7.5 mg (calculated per piece of gum), such as about 1.0 to about 6.0 such as about 2.0 to about 6.0 or about 2.0 to about 5.0 mg, or about 3.0 to about 6.0 or about 3.0 to about 5.0, such as 1.0, 1.25, 1.5, 1.75, 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, 7.0 7.25, or 7.5 mg.

In one example sodium carbonate or sodium bicarbonate may be present in an amount of 0.5 mg to about 3.5 mg, such as 0.5 mg to 2.5 mg, such as 0.5 mg to 1.0 mg or 0.5, 1.0, 1.5, 2.0, or 2.5 mg and trometamol base (Tris base), or the corresponding conjugated acid of trometamol such as Trometamol hydrochloride (Tris HCl), may be present in an amount of 1.5 mg to 5.0 mg, such as 2.0 to 5.0, 3.0 mg to 5.0 mg or 1.5, 2.0, 2.5, 3.0, 3.5, 4.0, 4.5 or 5.0 mg.

The gum core is coated with an outer polyol-based hard coating and may further include one or more polymer based film coatings.

The individually film coatings may have a thickness of from about 20 μm to about 200 μm, such as 20 μm to about 100 μm, such as 20 μm to 60 μm, such as 30 μm.

The film forming polymers may be chosen among hydroxy propyl methyl cellulose (HPMC), methyl hydroxy ethyl cellulose (MHEC), hydroxy propyl cellulose (HPC), hydroxyethyl cellulose (HEC), methacrylic acid copolymer-type C, sodium carboxy methyl cellulose, hydroxypropyl methylcellulose phthalate, (HPMCP), ethyl hydroxyl ethyl cellulose (EHEC), and other film forming polymers such as, polydextrose, polyethylene glycols, acrylate polymers, polyvinyl alcohol-polyethylene glycol graft copolymers, complex of polyvinylpyrrolidone (PVP), such as povidone, polyvinyl alcohol (PVOH or PVA), microcrystalline cellulose, carrageenan, pregelatinized starch, polyethylene glycol, and combinations thereof.

In one embodiment, the film-forming polymers are selected among hydroxy propyl methyl cellulose (HPMC), methyl hydroxy ethyl cellulose (MHEC), hydroxy propyl cellulose (HPC), hydroxyethyl cellulose (HEC), ethyl hydroxyl ethyl cellulose (EHEC) and polyvinyl alcohol (PVOH or PVA).

If two polymer based film coatings are applied, the same as well as different polymers and mixtures thereof could be used in the separate coatings. Examples includes such as when both film layers are based on hydroxy propyl methyl cellulose (HPMC) or one is based on hydroxy propyl methyl cellulose (HPMC) an the other one is based on another film forming polymer such as polyvinyl alcohol (PVOH or PVA). The film forming polymers may display somewhat different characteristics. For example, PVA is regarded to be more resistant against elevated pH and could thus be suitable to be used for the buffer containing film coating when there is an aim for a high pH.

HPMC provides a nice palatability as well as being able to provide a prolonged boost of flavor and sweetener when applied to a hard-coated nicotine chewing gum.

The polyol-based hard coating outside the film coating comprises at least one sugar alcohol or mixtures thereof. The sugar alcohol may be erythritol, maltitol, xylitol, lactitol, isomalt, mannitol, arabitol, isomalt and sorbitol or mixtures thereof. The polyol-based hard coating may have a thickness of from about 350 μm to about 750 μm, such as 500 μm. In one embodiment, the polyol-based hard coating is a mixture of xylitol and maltitol or contains xylitol only.

Examples of flavoring agents/flavors include, fruit and berry flavors such as lime, orange, lemon, black current, blood orange, cranberry, cloudberry, goji berry, raspberry, strawberry, wild strawberry, sea buckthorn, cherry, melon, kiwi, papaya, pineapple, passion fruit, coconut, and other flavors such as honey, herbs, the, anise, water grass, lemon grass, cooling agent, ginger, coffee, eucalyptus, mangostan, peppermint, spearmint, wintergreen, tutti-frutti, cinnamon, cacao/cocoa, vanilla, liquorice, salt, pepper, chili, menthol, aniseeds, or mixtures thereof. The flavoring agents/flavors may be natural extracts as well as synthetic and semisynthetic versions as well as mixtures of flavors. The flavors may be the same or different and can be present in the gum core, film coating(s), polyol-based hard coating as well as in the outer portion(s)/layer(s). Suitable examples of flavors are mint family flavors, fruit and berry flavors.

In addition, the chewing gum may have at least one artificial sweetener. The at least one artificial sweetener may be present in the gum core, film coating(s) or polyol-based hard coating and/or in the outer portion(s)/layer(s). Examples of artificial sweeteners are saccharin, sodium saccharin, aspartame, acesulfame K, neotame, thaumatin, glycyrrhizin, sucralose, cyclamate, dihydrochalcone, alitame, miraculin and monellin and mixtures thereof.

Fused onto the polyol-based hard coating is at least one portion/layer. The at least one portion comprises nicotine salt and at least one sugar alcohol or mixture of sugar alcohols. The portion may also include at least one sweetener and/or at least one flavor, such as those mentioned above. Nicotine salt in the at least one portion/layer is intended to include nicotine in a readily dissolvable form.

In one embodiment another at least one portion/layer comprising at least one buffer and at least one sugar alcohol or mixture of sugar alcohols, wherein the buffer(s) are in an amount of from about 3 mg to about 7.5 mg is/are fused onto a hard-coated chewing gum. The at least one portion/layer may also include at least one sweetener and/or at least one flavor, such as those mentioned above.

The at least one portion/layers may have the same size and weight or different size and weight, being placed on top of each other, beside each other or on different sides of the chewing gum. The at least one portion/layer comprising nicotine or buffer(s) may be placed on top of each other, beside each other if the at least one portion/layer is dries and solidified completely or on opposite sides of the chewing gum.

The above mentioned at least one portion/layer may comprise a mixture of erythritol and xylitol in a proportional amount of about 90:10, 91:9, 92:8, 93:7, 96:4, 95:5, 96:4, 97:3, 98:2, 99:1 or 100:0 (% w/w of erythritol:xylitol). In another embodiment, the portion comprises at least erythritol.

The nicotine is evenly distributed in the nicotine containing at least one portion/layer outside the hard-coated gum. In those embodiments wherein there are at least one portion/layer outside the hard-coated gum comprising buffer(s), the buffer(s) is/are evenly distributed in the at least one portion/layer.

Nicotine salts in the at least one portion/layer on the outside of the hard coated chewing gum may be present in an amount of about 0.25 to about 2.5 mg, such as 0.5 to about 1 mg or 0.25, 0.5, 0.75, 1.0, 1.25, 1.5, 1.75, 2.0, 2.25 or 2.5 mg. In addition, the total weight of the portion(s)/layer(s) is about 2-10% such as 2-5% of the total weight of the chewing gum.

In another embodiment, the at least one portion/layer comprising one or more buffer(s) could include a combination of erythritol and xylitol or erythritol. Such portion(s)/layer(s) may have a total weight of the portion(s) or layer(s) up to 10% or even up to 15% of the total weight of the chewing gum.

When the buffer(s) is/are present in the portion/layer outside the hard-coated gum, the buffer(s) may be present in a total amount of from about 3 mg to about 7.5 mg for each chewing gum, such as about 3 mg to about 5 mg, such as 3.0, 3.25, 3.5, 3.75, 4.0, 4.25, 4.5, 4.75, 5.0, 5.25, 5.5, 5.75 6.0, 6.25, 6.5, 6.75, 7.0 7.25, 7.5, or 7.5 mg.

In another embodiment the invention relates to a new chewing gum comprising at least a gum core comprising nicotine polacrilex, at least one first film coating comprising polyvinyl alcohol (PVA) which comprises at least two buffers wherein one buffer is sodium carbonate or sodium bicarobonate and the other is trometamol base (Tris base) and/or Trometamol conjugated acid such as Trometamol hydrochloride (Tris conjugated acid), and a second film coating comprising HMPC and at least one flavor and at least one sweetener, at least one outer hard polyol coating covering the film coatings comprising at least xylitol, and at least one portion/layer fused onto the outer polyol hard coating, wherein the at least one portion/layer is based on erythritol and comprising a nicotine salt, such as nicotine bitartrate or nicotine ditartrate dihydrate (could also be referred to as nicotine hydrogen tartrate (NHT) or nicotine bitartrate).

The outer polyol-based at least one portion/layer may be colored. The coloring agents include lakes and dyes being approved as a food additive and examples of coloring agents are artificial colors or natural colors. One example is when the portion is defined above and may be a dot, like the dots on a lady bird.

Examples of artificial colors approved for food use in the EU include: E104: Quinoline, Yellow, E122: Carmoisine, E124: Ponceau 4R, E131: Patent Blue V and E142: Green S. In the US, the following seven artificial colorings are generally permitted in food: FD&C Blue No. 1—Brilliant Blue FCF, E133 (blue shade), FD&C Blue No. 2—Indigotine, E132 (indigo shade), FD&C Green No. 3—Fast Green FCF, E143 (turquoise shade), FD&C Red No. 3—Erythrosine, E127 (pink shade, commonly used in glace cherries), FD&C Red No. 40—Allura Red AC, E129 (red shade), FD&C Yellow No. 5—Tartrazine, E102 (yellow shade), FD&C Yellow No. 6—Sunset Yellow FCF, E110 (orange shade) or iron oxide.

Examples of natural colors includes: Carotenoids (E160, E161, E164), chlorophyllin (E140, E141), anthocyanins (E163), and betanin (E162), Annatto (E160b), a reddish-orange dye made from the seed of the achiote, Caramel coloring (E150a-d), made from caramelized sugar, Carmine (E120), a red dye derived from the cochineal insect, Dactylopius coccus, Elderberry juice (E163), Lycopene (E160d), Paprika (E160c) and Turmeric (E100), Titanium dioxide or iron oxide.

In addition, the chewing gum may have at least one artificial sweetener. The at least one artificial sweetener may be present in the gum core, film coating(s), polyol-based hard coating and/or in the outer one or more portion(s)/layer (s). Examples of artificial sweeteners are saccharin, sodium saccharin, aspartame, acesulfame K, neotame, thaumatin, glycyrrhizin, sucralose, cyclamate, dihydrochalcone, alitame, miraculin and monellin and mixtures thereof.

The at least one outer portion/layer, may have a total weight of about 1-10% of the total gum weight, such as 2-10%, such as 2-3%, 1.5, 2.0, 2.5, 3.0, 3.5, 4.0, 4.5, 5.0% or even up to 15% or even up to 20% of the total weight of the chewing gum.

The nicotine polacrilex present in the chewing gum core may be in an amount from about 1.0 to about 6.0 mg, about 2.0 to about 4.0 mg, such as 1.0, 1.25, 1.5, 1.75, 2.0, 2.25, 2.5, 2.75, 3.0, 3.25, 3.5, 3.75, 4.0, 4.5, 5.0, 5.5 or 6.0, calculated as the free base per piece of gum and the nicotine salt present in the outer at least one portion/layer may be in an amount of from about 0.25 to about 2.5 mg, such as 0.25, 0.3, 0.35, 0.4, 0.45, 0.5, 0.55, 0.6, 0.65, 0.7, 0.75, 0.8, 0.85, 0.9, 0.95, 1.0, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45 or 2.5 mg, such as 0.25 to 1.0 mg or 0.25 to 1.5 or 0.25 to about 2.5 mg (calculated as the free base).

The relative amount of nicotine salt in relation to the buffer(s) located outside the gum core or located outside the hard coated gum is important since the buffer(s) will enable a conversion of the nicotine salt to its free base form in order to promote a fast uptake of nicotine.

If too little buffer(s) in relation to the nicotine salt is available, the conversion of nicotine to its free base form will be affected, which may lead to a relatively higher portion of the nicotine in its acidic form which will result in a lower fraction of nicotine to be adsorbed into the oral mucosa, and instead being subject to transportation into the gastrointestinal tract and exposure to the so called first-pass metabolism. This could lead to a comparably slower and reduced absorption of nicotine, affecting the nicotine concentrations in the systemic circulation and a comparably slower (and lower) craving relief.

In some embodiment(s) at least one outer portion/layer on the hard-coated gum comprises nicotine bitartrate or nicotine ditartrate dihydrate in an amount of from 0.25 mg to 2.5 mg nicotine (calculated as free base), as well as one or more buffer(s) which are located either in another portion/layer on the outside of the hard-coated gum or in a film coating outside the gum core, wherein the buffer(s) comprises sodium carbonate and/or Sodium bicarbonate in an amount of from 0.5 mg to 3.5 mg and trometamol base form as mentioned above, in an amount of from 1.5 mg to 5.0 mg.

Manufacturing of a Nicotine Chewing Gum.

The invention also relates to a method of manufacturing a chewing gum using steps such as mixing, rolling and scoring, film- and hard coating and deposition/fusing of one or more polyol-based portions on the gum surface through screen printing, melt lamination, ink-printing, pipetting or 3-D printing where the following steps could be used.

Step A. Providing a chewing gum core comprising nicotine, such as nicotine polacrilex, wherein the chewing gum may be manufactured as shown by the processes and the examples disclosed in U.S. Pat. No. 3,877,468.

STEP B. Providing a polymer based film coating formulation comprising sweeteners and flavors and applying the film coating to the core of the chewing gum using for example commercially available film coating equipment suitable for aqueous formulations, allowing the coating to dry on the chewing gum using for example air, such as dry and temperature controlled air to obtain a film coated chewing gum.

STEP C. Providing a polymer based film formulation comprising at least two buffers and optionally also at least one sweetener and at least one flavor, coating said chewing gum with the film using for example commercially available film coating equipment, suitable for aqueous formulations, allowing the coating to dry on the chewing gum using for example air, such as dry and temperature controlled air and obtaining a film coated chewing gum.

STEP B could be omitted when there is a STEP C. STEP C could be omitted when STEP G is included. Step B and STEP C could come in any order if included.

Step E. Providing a polyol-based hard coating formulation comprising at least one sugar or a mixture of sugar alcohol as defined above and coating the gum with a polyol-based hard coating formulation and obtaining an outer coated chewing gum using for example commercially available hard coating equipment, suitable for aqueous formulations, allowing the coating to dry on the chewing gum using for example air, such as dry and temperature controlled air dry air and temperature control and to obtain a hard-coated chewing gum.

Step F. Providing a composition comprising nicotine salt, such as the monotartrate, hydrogen tartrate, citrate, malate, hydrochloride, nicotine bitartrate or nicotine bitartrate dihydrate salt of nicotine and at least one sugar alcohol or a mixture of sugar alcohols, such as erythritol, maltitol, xylitol, lactitol, isomalt, mannitol, arabitol, isomalt and sorbitol or mixtures thereof, and fusing said composition onto said hard-coated chewing gum as one or more portion(s) or layer(s) located outside the hard-coated gum and, obtaining a chewing gum with outer nicotine portion(s) or layer(s) through screen printing, melt lamination, ink-printing, pipetting or 3-D printing.

Step G. Providing a composition comprising one or more buffer(s) and at least one sugar alcohol or a mixture of sugar alcohols and fusing said composition onto said chewing gum as one or more portion(s) or layer(s) through screen printing, melt lamination, ink-printing, pipetting or 3-D printing and to obtain a hard-coated gum with one or more portion(s) or layer(s) comprising nicotine salt and with one or more portion(s) or layer(s) comprising one or more buffer(s).

The different components and ingredients to be included in the manufacturing process could be found above.

Finally, the invention relates to the use of above defined chewing gums for the treatment of a human beings suffering from cravings from tobacco dependency and/or e-cigarette dependency.

EXAMPLES

Specific embodiments of the present invention are illustrated by way of the following examples. This invention is not confined to the specific limitations set forth in these examples.

The amounts of the ingredients are expressed in different ways in the examples and not consistent with what will result in a final chewing gum. However, for a person skilled in the art it is obvious how to recalculate and develop a chewing gum according to the disclosure.

Example 1 Chewing Gum with One Polymer Film Coating with One or More Buffers Chewing gum base was obtained from a commercial chewing gum base producer and preparation of chewing gums with nicotine polacrilex was made according to the one or more of the processes/examples disclosed in U.S. Pat. No. 3,877,468. WO2006/124366 discloses the process to formulate and manufacture nicotine gums with polymer based film containing inside a polyol-based hard coating.

The following film forming compositions were used to obtain a film coating in this example. Compositions are presented as mg per piece of gum.

| Examples | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Hydroxypropylmethylcellulose (HPMC) | 7,5 | 9 | 7,5 | 13 | 15 | | 9 | 9 | 9 | | | | 11 | 11 | 9 | 11 | 13 | 26 | 7,5 | 9 |
| Polyvinylalcohol (PVA) | | | | | | 7,5 | | | | 8 | 8 | 8 | | | | | | | | |
| Polysorbate 80 | 0,5 | 0,5 | 0,5 | 0,5 | 0,5 | 0,5 | 0,5 | 0,5 | 0,5 | 0,5 | 0,5 | 0,5 | 0,5 | 0,5 | 0,5 | 0,5 | 0,5 | 1,0 | 0,5 | 0,5 |
| Sucralose | 5 | 5 | 5 | 5 | 5 | 5 | 5 | 5 | 5 | 5 | 5 | 5 | 5 | 5 | 5 | 5 | 5 | 10 | 5 | 2,5 |
| Flavor | 9 | 9 | 9 | 9 | 9 | 9 | 9 | 9 | 9 | 9 | 9 | 9 | 9 | 9 | 9 | 9 | 9 | 18 | 9 | 10 |
| Sodium carbonate | | | 1 | 1,25 | 3,5 | | 1 | | 0,5 | | 0,25 | 0,5 | 0,25 | 1 | 1 | 1,5 | 1,25 | 3 | 1 | 1 |
| Sodium bicarbonate | 1 | 1 | | 1,25 | | | | 0,5 | 0,5 | 1 | 0,75 | | 1,75 | 3 | 0,25 | 1,5 | 2,75 | 4 | | |
| Trometamol base | 2 | 3 | 3 | 1 | 1 | 3 | 5 | 5 | 5 | 5 | 5 | 5 | 3 | | 1,75 | | | | | |
| Purified water[1] | q.s. | q.s. | q.s. | q.s. | q.s. | q.s. | q.s. | q.s. | q.s. | q.s. | q.s. | q.s. | q.s. | q.s. | q.s. | q.s. | q.s. | q.s. | q.s. | q.s. |
| Hydrochloric acid (10%) or NaOH (0.1 M)[2] | ad pH 9,5 | ad pH 9,5 | ad pH 10 | ad pH 10,5 | ad pH 10,5 | ad pH 9,5 | ad pH 10 | ad pH 9 | ad pH 10 | ad pH 9 | ad pH 9 | ad pH 10,5 | ad pH 9 | ad pH 10 | ad pH 9,5 | ad pH 10,5 | ad pH 10 | ad pH 10,5 | ad pH 10 | ad pH 10,5 |

[1] Majority of purified water is removed during film coating process
[2] Coating preparation is pH adjusted with Hydrochloric (10%) acid or NaOH (0.1 M) to target pH For the polymer coating process the dry content of coating preparation can be varied between 20-50 w/w % to facilitate the incorporation of various of amounts of buffering agents. Adapting dry content with various of amount buffering agent will facilitate coating preparation without salting out the polymer.

Example 2 Chewing Gum with Two Polymer Film Coatings, One with Two or More Buffer and One with Flavors and Sweeteners Chewing gum base was obtained from a chewing gum base producer and preparation of chewing gum cores with nicotine polacrilex was made according to one or more of the processes/examples disclosed in U.S. Pat. No. 5,976,581. WO2006/124366 discloses a polymer based film coating inside a polyol-based hard coating. The chewing gums were coated with two different polymer based film coatings as shown in the table below. Compositions are presented as mg per piece of gum.

| | Examples | 1 | 2 | 3 | 4 | 5 | 6 | 7 | 8 | 9 | 10 |
|---|---|---|---|---|---|---|---|---|---|---|---|
| Polymer coating A | Polyvinylalcohol (PVA) | 7,5 | 8 | 8 | 8 | 8 | 9 | 10 | 8 | 10 | 9 |
| | Sodium carbonate | | | | | 1 | 2,5 | 1,5 | 2,5 | 1,5 | 2,5 |
| | Sodium bicarbonate | 1 | 1 | 0,5 | 0,5 | | 2,5 | 1,5 | 2,5 | 1,0 | 2,5 |
| | Sodium hydrogen phosphate | | | | 0,5 | 1 | | | 5 | 5 | 2 |
| | Trometamol | 3 | 5 | 5 | 5 | 5 | 7 | 5 | | | |
| | Purified water[1] | q.s. | q.s. | q.s. | q.s. | q.s. | q.s. | q.s. | q.s. | q.s. | q.s. |
| | Hydrochloric acid (10%)[2] | ad pH 9,5 | ad pH 9,5 | ad pH 10,5 | ad pH 9 | ad pH 10,5 | ad pH 10,5 | ad pH 10,7 | ad pH 10,5 | ad pH 10,7 | ad pH 10,5 |
| Polymer coating B | Hydroxypropylmethylcellulose (HPMC) | 7,5 | 8 | 9 | 7,5 | 7,5 | 9 | 9 | 8 | 10 | 10 |
| | Polysorbate 80 | 0,5 | 0,5 | 0,5 | 0,5 | 0,5 | 0,5 | 0,5 | 0,5 | 0,5 | 0,5 |
| | Sucralose | 4 | 5 | 5 | 4 | 4 | 4,9 | 5 | 5 | 5,3 | 5,2 |
| | Flavor | 9 | 8 | 9 | 7 | 9 | 9 | 9 | 8 | 9,3 | 9,2 |
| | Purified water[1] | q.s. | q.s. | q.s. | q.s. | q.s. | q.s. | q.s. | q.s. | q.s. | q.s. |

[1] Majority of purified water is removed during film coating process
[2] Coating preparation is pH adjusted with Hydrochloric (10%) acid or NaOH (0.1 M) to target pH Dry content of coating preparation can be varied between 20-50 w/w % to facilitate the incorporation of various of amounts of buffering agents.

Example 3 Formulation of Nicotine Salt Compositions for Outer Portion(s) or Layer(s)

Preparation of different portions containing nicotine salt and excipients.

| | Examples | | | | | | | | |
|---|---|---|---|---|---|---|---|---|---|
| | 1 | 2 | 3 | 4 | 5 | 6 | 7 | 8 | 9 |
| | Amounts expressed in %w/w for each component per example | | | | | | | | |
| APIs | | | | | | | | | |
| Nicotine Bitartrate Dihydrate | 15,39 | 15,4 | 14,3 | 14,3 | 14,3 | 14,3 | 14,3 | 7,13 | 15,35 |
| Excipients | | | | | | | | | |
| Xylitol | | 82,8 | 80,4 | | 82,4 | 20,0 | 3,9 | | |
| Isomalt | 84,61 | | | | | | | | |
| Erythritol | | | 3,3 | 83,7 | | 65,7 | 79,8 | 92,7 | 84,65 |
| Dye | q.s. | q.s. | q.s. | q.s. | q.s. | q.s. | q.s. | q.s. | q.s. |
| Mannitol 25 μ | | | | | 3,3 | | | | |
| Sodium Carbonate | | | | | | | | | |
| Neo tame | | | | | | | 0,15 | | |
| Titanium dioxide | | 1,8 | 2,0 | 2,0 | | 2 | | | |

Manufacturing: all starting materials, polyols or mixtures of several polyols, nicotine source and dye, seeding agent or sweetener, if applicable where mixed in a glass beaker. The mixture was heated until melting under stirring of all the components except for titanium dioxide. 20 to 40 mg of the melted mass was deposited on the chewing gum with aid of a micropipette. The droplet was occasionally flattened with a heated tool directly after deposition to reduce the thickness of the deposited droplet.

Use of Xylitol as the primary polyol gave too long solidification times to be utilized in commercial manufacturing. Use of seeding agents (Mannitol 25μ or Titanium dioxide) did not shorten the solidification time. Isomalt had very fast solidification time but very high melting point (153° C.) which is not desirable from stability and safety perspective. Erythritol exhibited fast solidification and much lower melting temperature (121.5° C.).

Example 4 Formulation of Compositions for Outer Portion(s) or Layer(s) Including Buffers

| | 1 | 2 | 3 | 4 | 5 |
|---|---|---|---|---|---|
| Erythritol (g) | 29,25 | 28,875 | 28,5 | 27,00 | 26,75 |
| Trometamol (g) | 0,75 | 1,125 | 1,5 | 3,00 | 3,75 |

-continued

| | 1 | 2 | 3 | 4 | 5 |
|---|---|---|---|---|---|
| Na$_2$CO$_3$ (g) | 0,75 | 0,75 | 0,75 | 0,75 | 0,75 |
| Total (g) | 30,75 | 30,75 | 30,75 | 30,75 | 30,75 |

All example formulations 1 to 5 gained a clear solution upon gentle manual mixing and melting at 125° C. without any remaining residue particles by visual control. Solidification time upon deposition of portions on the chewing gum was prolonged with increasing concentration of Trometamol but within limits for manufacturability.

Manufacturing: all starting materials, polyol and buffer(s) where mixed in a glass beaker. The mixture was heated until melting under stirring of all the components. 20 to 40 mg of the melted mass was fused on the chewing gum with aid of a micropipette. The droplet was occasionally flattened with a heated tool directly after deposition to reduce the thickness of the deposited droplet.

The invention claimed is:

1. A nicotine chewing gum comprising:
   i. a gum core comprising nicotine,
   ii. a polymer-based film coating comprising at least one flavor and at least one sweetener covering the gum core,
   iii. a polyol-based hard coating covering the polymer-based film coating, comprising at least one sugar alcohol,
   iv. a first portion/layer fused onto an outside of the polyol-based hard coating, wherein the first portion/layer comprises a nicotine salt and at least one sugar alcohol,
   v. a second portion/layer fused onto an outside of the polyol-based hard coating, wherein the second portion/layer comprises one or more buffer(s) in an amount of from about 3 mg to about 7.5 mg and at least one sugar alcohol, and
   wherein a nicotine release from the first portion/layer (iv) is immediate and a nicotine release from the gum core (i) is extended,
   wherein the one or more buffer(s) (v) outside the gum core promotes a rapid uptake of nicotine from the first portion/layer (iv) through an oral mucosa, and
   wherein both the first and second portions/layers are located either: a) not beside each other and fused onto different sides of the polyol based hard coating, or b) are both fused onto the same side of the polyol based hard coating.

2. The chewing gum according to claim 1, wherein the at least one sugar alcohol in the first and/or second portion/layer is erythritol.

3. A nicotine chewing gum comprising,
   i. a gum core comprising nicotine,
   ii. a film coating covering the gum core comprising at least two buffers and at least one film forming polymer,
   iii. a polyol-based hard coating covering the film coating, wherein the polyol-based hard coating comprises at least one sugar alcohol,
   iv. a portion/layer fused onto an outside of the polyol-based hard coating, wherein the portion/layer comprises a nicotine salt and at least one sugar alcohol, and
   wherein a nicotine release from the portion/layer (iv) is immediate and a nicotine release from the gum core (i) is extended,
   wherein the at least two buffers (ii) in the film coating outside the gum core promotes a rapid uptake of nicotine from the portion/layer (iv) through an oral mucosa, and
   wherein either a) the portion/layer is fused onto one side of the polyol-based hard coating, b) the portion is in a form consisting of a round portion, a square portion, a conic portion, a triangle portion, or a trademark, or c) the portion/layer covers 40% of the gum surface.

4. The nicotine chewing gum according to claim 3, wherein the film coating further comprises at least one sweetener and at least one flavor.

5. The nicotine chewing gum according to claim 3, comprising at least two film coatings covering the gum core, wherein a first film coating comprises at least two buffers and at least one film forming polymer, and a second film coating comprises at least one sweetener, at least one flavor, and at least one film forming polymer.

6. The nicotine chewing gum according to claim 3, wherein the at least one film forming polymer in the film coating is selected from the group consisting of hydroxy propyl methyl cellulose (HPMC), methyl hydroxy ethyl cellulose (MHEC), hydroxy propyl cellulose (HPC), hydroxyethyl cellulose (HEC), ethyl hydroxyl ethyl cellulose (EHEC), polyvinyl alcohol (PVOH or PVA) or a mixture thereof.

7. The nicotine chewing gum according to claim 5, wherein the at least one film forming polymer in the first film coating comprises PVA and the at least one film forming polymer in the second film coating comprises HPMC.

8. The nicotine chewing gum according to claim 3, wherein the at least one sugar alcohol in the portion/layer is erythritol.

9. The nicotine chewing gum according to claim 3, wherein the at least two buffer(s) are selected from the group consisting of sodium carbonate, sodium bicarbonate, potassium carbonate, potassium bicarbonate, trometamol base (Tris base) or the corresponding conjugated acid of trometamol such as Trometamol hydrochloride (Tris HCl), trisodium phosphate, disodium hydrogenphosphate, sodium dihydrogen phosphate, tripotassium phosphate, dipotassium hydrogenphosphate, potassium dihydrogen phosphate, and mixtures thereof.

10. The nicotine chewing gum according to claim 9, wherein the at least two buffer(s) are selected from the group consisting of sodium carbonate, sodium bicarbonate, trometamol base (Tris base) or the corresponding conjugated acid of trometamol such as Trometamol hydrochloride (Tris HCl), or mixtures thereof.

11. The nicotine chewing gum according to claim 3 wherein the at least two buffers in the film coating outside the gum core are present in an amount from about 1.0 to about 7.5 mg per piece of gum.

12. The nicotine chewing gum according to claim 3, wherein the nicotine in the gum core is nicotine polacrilex and the nicotine salt in the portion/layer is nicotine bitartrate or nicotine ditartrate dihydrate.

13. The nicotine chewing gum according to claim 3, wherein the gum core comprises nicotine polacrilex in an amount of from about 1.0 mg to about 7.5 mg (calculated as the free base) and the nicotine salt in the portion/layer is present in an amount of from about 0.25 mg to about 2.5 mg per piece of gum (calculated as the free base).

14. The nicotine chewing gum according to claim 3, wherein
   i. the nicotine salt comprises nicotine bitartrate or nicotine ditartrate dihydrate in an amount of from 0.25 mg to 2.5 mg (calculated as the free base), and
   ii. the at least two buffers comprise Sodium carbonate and/or Sodium bicarbonate in an amount of from 0.5 mg to 3.5 mg, in addition to Trometamol-Base or the corresponding conjugated acid of trometamol such as Trometamol hydrochloride (Tris HCl) in an amount of from 1.5 mg to 5.0 mg.

15. A method of manufacturing a chewing gum, comprising the steps of;
   a. providing a gum core comprising nicotine,
   b. providing a polymer-based film coating formulation including at least one flavor and at least one sweetener,
   c. coating the gum core with the polymer-based film coating formulation,
   d. obtaining a polymer-based film coated chewing gum,
   e. providing a polyol-based hard coating formulation comprising at least one sugar alcohol, f. coating said polymer-based film coated chewing gum with said polyol-based hard coating formulation,
g. obtaining a polyol-based hard-coated chewing gum,
h. providing a composition comprising a nicotine salt and at least one sugar alcohol,
i. fusing said composition onto an outside of the polyol-based hard-coated chewing gum as at least one portion/layer and obtaining a hard-coated chewing gum with at least one portion/layer containing nicotine salt,
j. providing a composition comprising one or more buffer(s) in an amount of from about 3 mg to about 7.5 mg and at least one sugar alcohol,
k. fusing said composition onto the outside of the polyol-based hard-coated chewing gum as at least one portion/layer, and
l. obtaining a hard-coated nicotine chewing gum,
wherein a nicotine release from the at least one portion/layer is immediate and a nicotine release from the gum core is extended,
wherein the compositions of step h and step j are located either: a) not beside each other and fused onto different sides of the polyol based hard coating, or b) are both fused onto the same side of the polyol based hard coating, and
wherein the one or more buffer(s) promotes a rapid uptake of nicotine through an oral mucosa.

16. A method of treatment of a human suffering from cravings from tobacco and/or e-cigarette dependency, comprising administering the nicotine chewing gum according to claim 3 to the human.

* * * * *